US012669492B2

(12) United States Patent
Lan et al.

(10) Patent No.: US 12,669,492 B2
(45) Date of Patent: Jun. 30, 2026

(54) IN-SITU TESTING INSTRUMENT AND METHOD FOR SOIL MOISTURE IN A HOLE

(71) Applicants:Chang'an University, Xi'an (CN);
Institute of Geographic Sciences and Natural Resources Research, CAS,
Beijing (CN)

(72) Inventors: Hengxing Lan, Xi'an (CN); Weifeng Sun, Xi'an (CN); Mervyn Lan, Xi'an (CN); Changgen Yan, Xi'an (CN); Langping Li, Xi'an (CN); Han Bao, Xi'an (CN); Yuming Wu, Xi'an (CN)

( * ) Notice: Subject to any disclaimer, the term of this patent is extended or adjusted under 35 U.S.C. 154(b) by 359 days.

(21) Appl. No.: 18/536,304

(22) Filed: Dec. 12, 2023

(65) Prior Publication Data

US 2024/0345058 A1     Oct. 17, 2024

Related U.S. Application Data

(63) Continuation of application No. PCT/CN2023/121875, filed on Sep. 27, 2023.

(30) Foreign Application Priority Data

Apr. 17, 2023     (CN) .......................... 202310402921.X

(51) Int. Cl.
G01N 33/24 (2006.01)
G01N 35/00 (2006.01)
(52) U.S. Cl.
CPC ..... G01N 33/246 (2013.01); G01N 35/00871 (2013.01)

(58) Field of Classification Search
CPC .................................................... G01N 33/246
See application file for complete search history.

(56) References Cited

U.S. PATENT DOCUMENTS

| | | | | |
|---|---|---|---|---|
| 3,729,284 A | * | 4/1973 | Hubmann | ............. B28B 1/0873 |
| | | | | 366/144 |
| 5,479,104 A | * | 12/1995 | Cambell | ............. G01N 27/048 |
| | | | | 324/663 |
| 5,644,947 A | * | 7/1997 | Hubbell | ............... G01N 33/246 |
| | | | | 73/73 |
| 10,053,985 B1 | * | 8/2018 | Peng | ....................... B09B 1/004 |

(Continued)

FOREIGN PATENT DOCUMENTS

| | | | |
|---|---|---|---|
| CN | 205474477 | * | 8/2016 |
| CN | 113186893 | * | 7/2021 |
| KR | 950004638 | * | 6/1995 |

*Primary Examiner* — John E Breene
*Assistant Examiner* — Alex T Devito

(57) ABSTRACT

An in-situ testing instrument for soil moisture in a hole includes a test bracket extended into a hole, a retracting and releasing mechanism used to drive the test bracket to rise and fall in the hole, a moisture test mechanism arranged on the test bracket, a plug-and-pull drive mechanism used to drive the moisture test mechanism to insert into soil on a side of the hole or to be pulled out by the soil on a side of the hole, and a signal receiving mechanism arranged on a ground, the signal receiving mechanism is electrically connected with the moisture test mechanism. The above-mentioned in-situ testing instrument and method for soil moisture in a hole can eliminate the steps of taking soil, packaging, weighing, and drying, and improve the test efficiency and the test accuracy.

16 Claims, 6 Drawing Sheets

(56)     References Cited

U.S. PATENT DOCUMENTS

2007/0079997 A1 *  4/2007  Chan ..................... B62D 57/00
                                                180/7.1
2012/0068688 A1 *  3/2012  Hill ..................... G01N 33/246
                                                29/428
2018/0352760 A1 *  12/2018  Haran ................. G01N 33/246

\* cited by examiner

13

22

IN-SITU TESTING INSTRUMENT AND METHOD FOR SOIL MOISTURE IN A HOLE

CROSS REFERENCE TO THE RELATED APPLICATIONS

This application is the Continuation application of International Application No. PCT/CN2023/121875, filed on Sep. 27, 2023, which is based upon and claims priority to Chinese Patent Application No. 202310402921.X, filed on Apr. 17, 2023, the entire contents of which are incorporated herein by reference.

TECHNICAL FIELD

The invention relates to the field of soil moisture testing technology, in particular to an in-situ testing instrument and method for soil moisture in a hole.

BACKGROUND ART

In the field of geotechnical engineering and geological engineering, it is necessary to test the soil moisture at different depths of the stratum to understand the moisture content of the soil, and then evaluate the shear and deformation resistance of the soil.

At present, the conventional methods for testing soil moisture at different depths of the stratum are still based on in-situ sampling of disturbed soil samples at different depths of the stratum and then weighing and drying in the room. However, those methods have the problems of low work efficiency and inaccurate soil moisture content test because it needs to take out the disturbed soil samples at different depths of the stratum and then encapsulate, weigh, and bake them.

SUMMARY

In order to solve the above problems, the invention provides an in-situ testing instrument and method for soil moisture in a hole. By in-situ testing the soil moisture content, the steps of soil collection, packaging, weighing, and drying are eliminated, which improves the test efficiency and accuracy.

In order to achieve the above purpose, the invention provides an in-situ testing instrument for soil moisture in a hole, comprising a test bracket extended into a hole, a retracting and releasing mechanism used to drive the test bracket to rise and fall in the hole, a moisture test mechanism arranged on the test bracket, a plug-and-pull drive mechanism used to drive the moisture test mechanism to insert into soil on a side of the hole or to be pulled out by the soil on a side of the hole, and a signal receiving mechanism arranged on a ground, the signal receiving mechanism is electrically connected with the moisture test mechanism.

Preferably, the test bracket comprises a first mounting plate, a second mounting plate, a third mounting plate, a fourth mounting plate, and a fifth mounting plate connected in turn by a screw from a bottom to a top;

a top of the fifth mounting plate is connected to a lifting rope of the retracting and releasing mechanism through a hanger.

Preferably, the retracting and releasing mechanism comprises a support fixed on the ground, a rotating shaft set inside the support, and a reel fixed on the rotating shaft at a position of a corresponding hole, one end of the rope is wound on the reel, and the other end of the rope is fixedly connected to the hanger;

one end of the rotating shaft that passes through the support is fixed with a handle.

Preferably, the moisture test mechanism comprises a mounting shell set slidingly on a second positioning plate, a moisture sensor fixed inside the mounting shell, and a probe fixedly connected to the moisture sensor at one end, and the other end of the probe extends out of the mounting shell.

Preferably, the plug-and-pull drive mechanism comprises a speed-regulating motor fixed at a top of the fourth mounting plate, a vertical gear shaft that is in a keyed connection with an output shaft of the speed-regulating motor at one end, a horizontal gear fixedly connected to the other end of the vertical gear shaft, and a horizontal gear placing frame in which an inner side meshes with an outer side of the horizontal gear;

the speed-regulating motor is electrically connected with a motor controller arranged on the ground.

Preferably, a center of the fourth mounting plate is equipped with a motor shaft hole;

a C-type guide groove is opened in the middle of the third mounting plate, and a C-type sliding groove is opened on the second mounting plate and corresponding to a position of the C-type guide groove, the C-type guide groove and the C-type sliding groove open in the same direction;

a groove wall of the C-type sliding groove is protruded from the C-type guide groove, a mounting shell is set horizontally and slidingly inside the C-type sliding groove, the horizontal gear placing frame is set slidingly inside the C-type guide groove at a top of the C-type sliding groove.

Preferably, weight-reducing holes are set at a center of the first mounting plate, two sides of the second mounting plate, two sides of the third mounting plate, two sides of the fourth mounting plate, and a center of the fifth mounting plate.

Preferably, an endoscope is fixed on a position on a screw where corresponding to the moisture sensor; the endoscope is electrically connected with an endoscope controller arranged on the ground, and the endoscope controller communicates with a monitoring terminal to observe a position of the moisture sensor.

Preferably, the signal receiving mechanism is a moisture sensor reader arranged on the ground.

A method of the in-situ testing instrument for soil moisture in a hole comprises the following steps:

S1, drilling a hole in an area to be detected;

S2, placing the retracting and releasing mechanism on the ground corresponding to the hole, and placing the test bracket inside the hole;

S3, turning on a power supply, using the handle to rotate the rotating shaft, and lowering the test bracket until the probe on the test bracket reaches a first test depth;

S4, controlling the rotation of the speed-regulating motor by the motor controller, driving the horizontal gear to rotate through the vertical gear shaft by the speed-regulating motor, and then driving the horizontal gear placing frame to move in a direction of the C-type guide groove towards a side wall of the hole, at the same time, driving the moisture sensor to move in a direction of the C-type sliding groove towards a side wall of the hole by the mounting shell, observing by the endoscope until the probe of the moisture sensor is inserted into the inside of the side wall of the hole, and stopping the speed-regulating motor from rotating, at this time, reading the moisture information of the soil at a current depth by the moisture sensor and transmitting the moisture information to the moisture sensor reader, after finishing reading, controlling the speed-regulating motor to rotate reversely by the motor controller, drawing back the probe to control the speed-regulating motor to stop running;

S5, rotating the rotating shaft again, lowering the test bracket until the probe on the test bracket reaches a second test depth, and repeating S4 until the test is completed.

The invention has the following beneficial effects:

The rapid test of soil moisture in situ test at different depths of the stratum is realized, which greatly improves the work efficiency.

The accuracy of the in-situ test of soil moisture at different depths of the stratum is realized, and the authenticity of the scientific research results is improved;

the test instrument is easy to carry, can be reused, and is convenient for long-term application.

The following is a further detailed description of the technical solution of the invention through drawings and an embodiment.

BRIEF DESCRIPTION OF THE DRAWINGS

Figure 1:
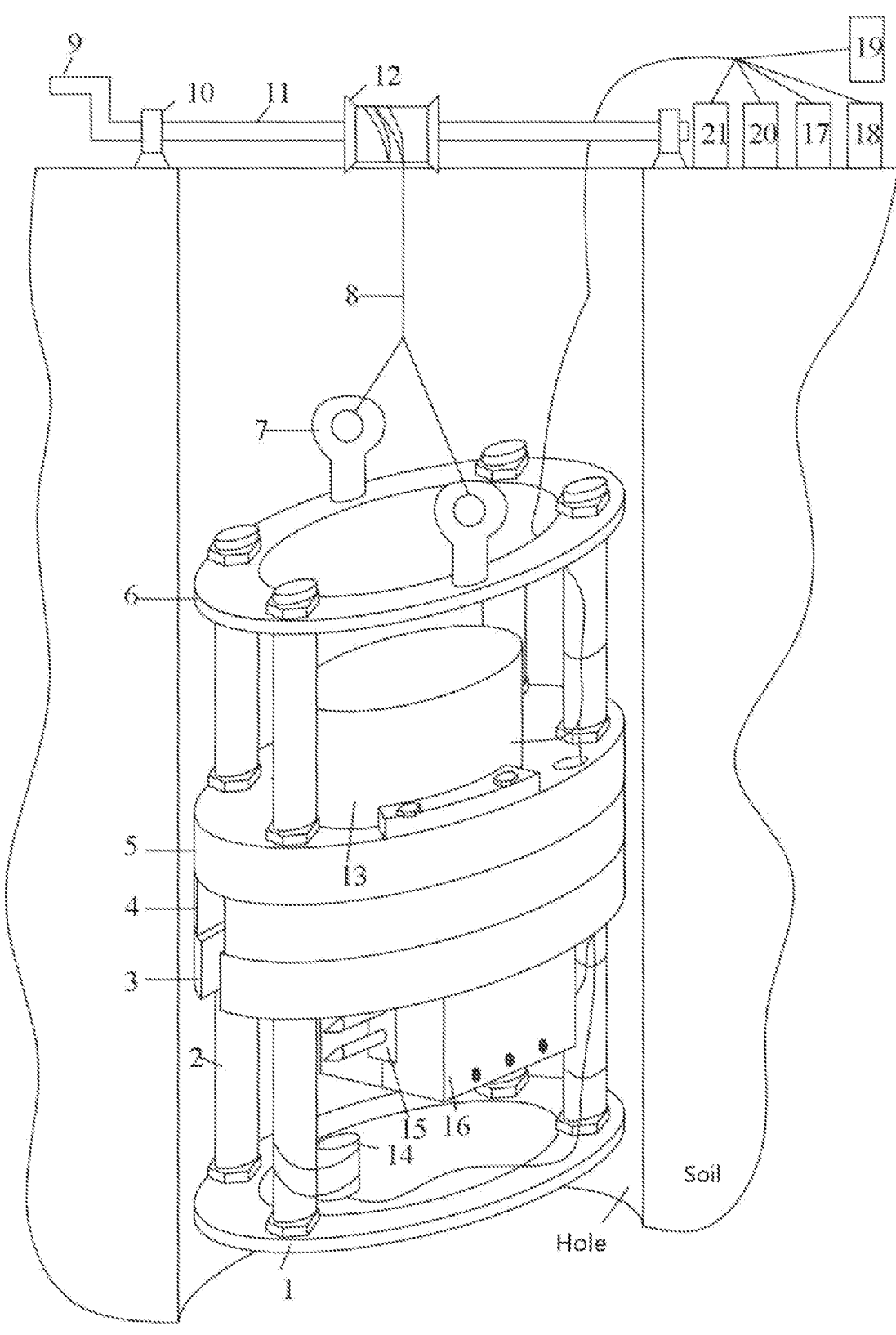
FIG. 1 is a structural schematic diagram of the in-situ testing instrument for soil moisture in a hole.
Figure 2:
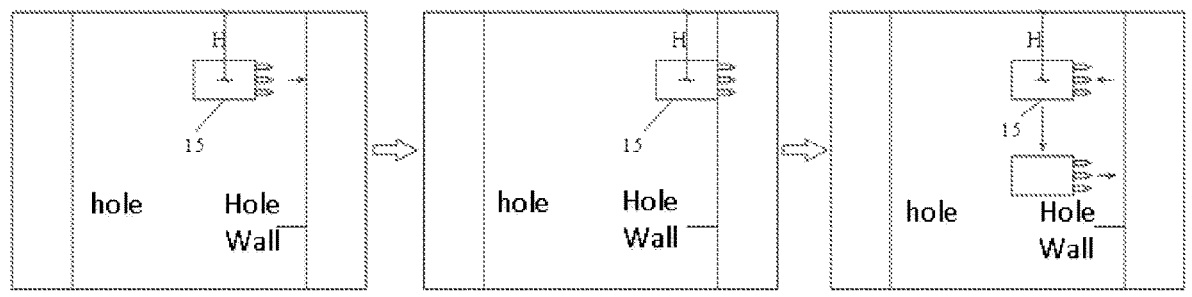
FIG. 2 is a test flow chart of the in-situ testing instrument and method for soil moisture in a hole;
Figure 3:
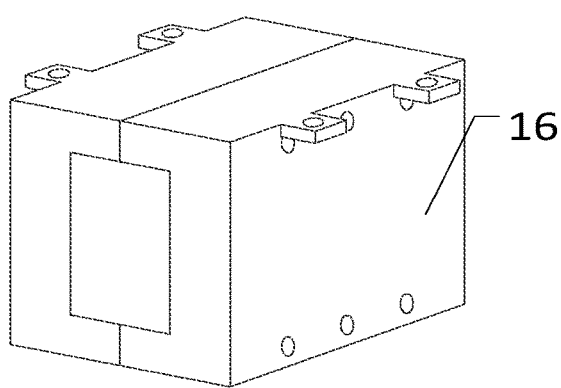
FIG. 3 is a structural schematic diagram of the mounting shell of the in-situ testing instrument for soil moisture in a hole.
Figure 4:
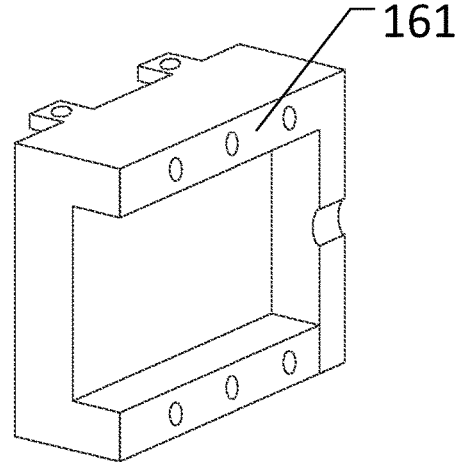
FIG. 4 is a structural schematic diagram of the left mounting semi-shell of the in-situ testing instrument for soil moisture in a hole.
Figure 5:
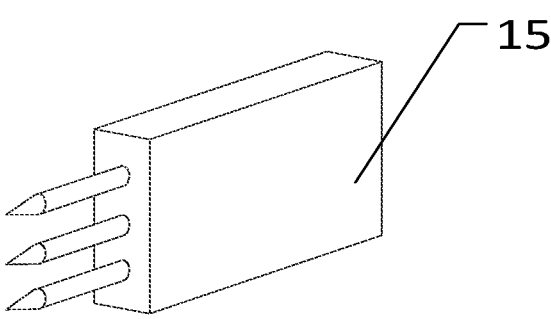
FIG. 5 is a structural schematic diagram of the moisture sensor of the in-situ testing instrument for soil moisture in a hole.
Figure 6:
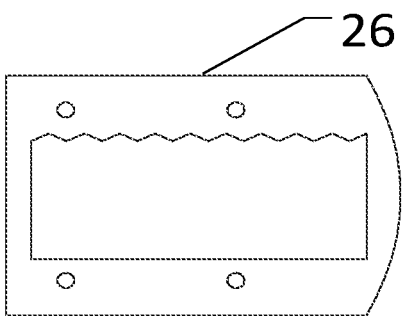
FIG. 6 is a structural schematic diagram of the horizontal gear placing frame of the in-situ testing instrument for soil moisture in a hole.
Figure 7:
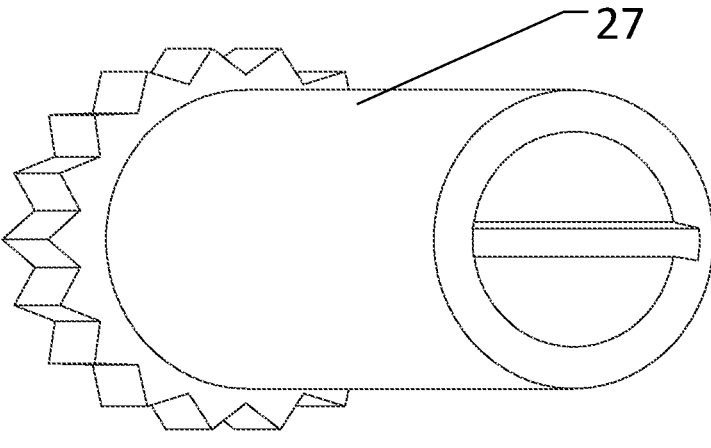
FIG. 7 is a structural schematic diagram of the horizontal gear of the in-situ testing instrument for soil moisture in a hole;
Figure 8:
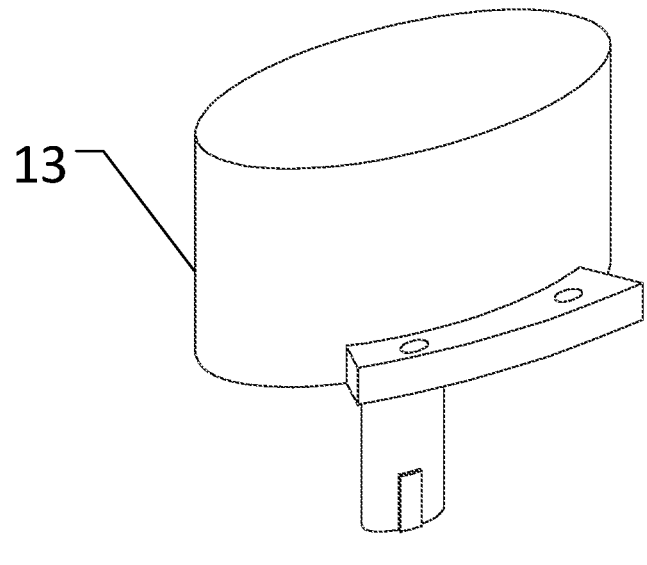
FIG. 8 is a structural schematic diagram of the speed-regulating motor of the in-situ testing instrument for soil moisture in a hole.
Figure 9:
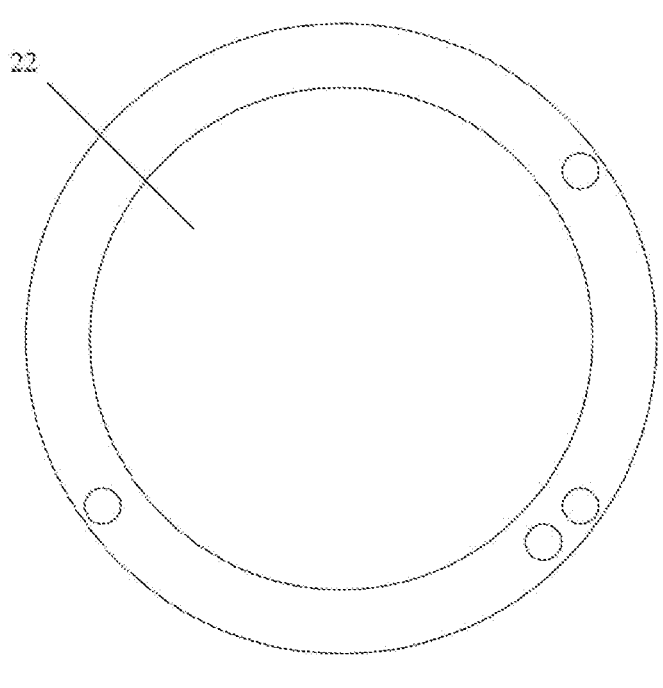
FIG. 9 is a top view of the first mounting plate of the in-situ testing instrument for soil moisture in a hole.
Figure 10:
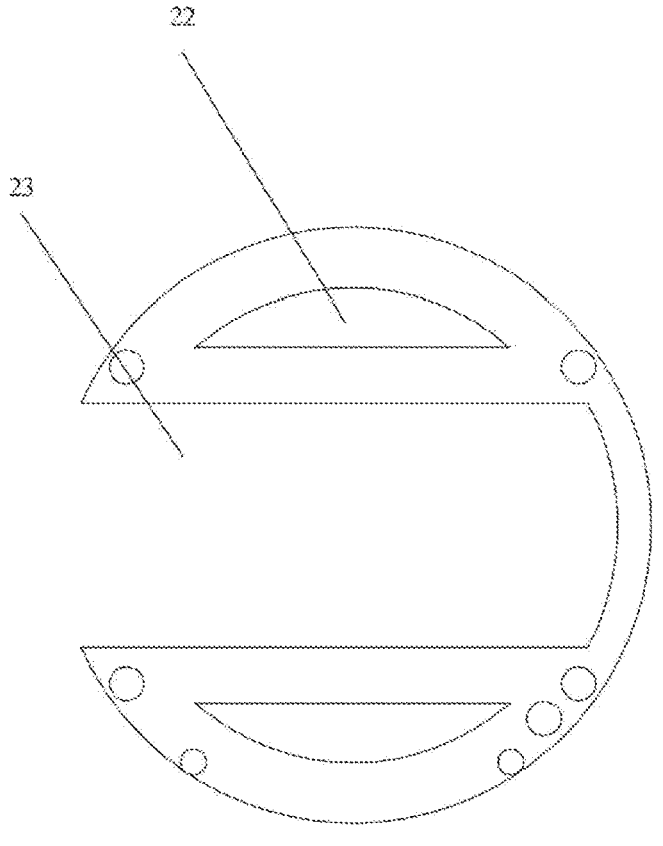
FIG. 10 is a top view of the second mounting plate of the in-situ testing instrument for soil moisture in a hole.
Figure 11:
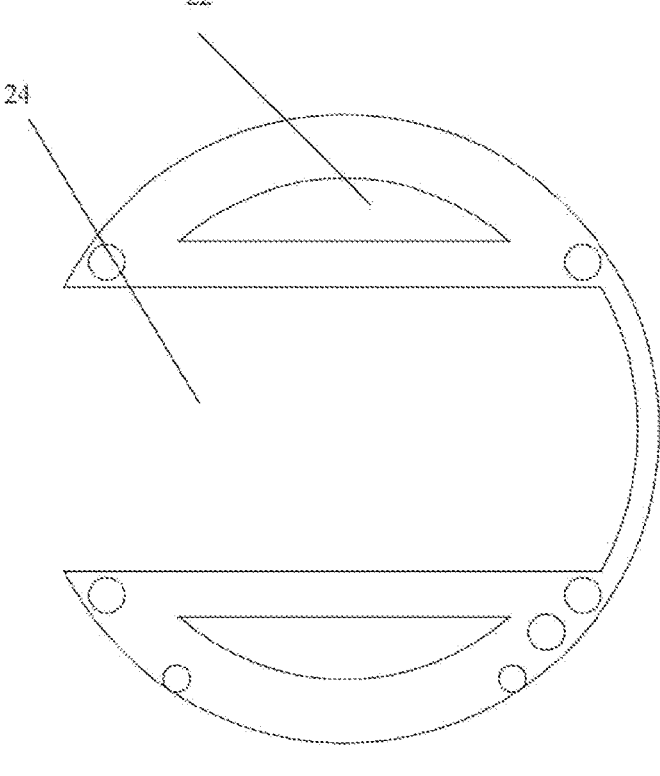
FIG. 11 is a top view of the third mounting plate of the in-situ testing instrument for soil moisture in a hole.
Figure 12:
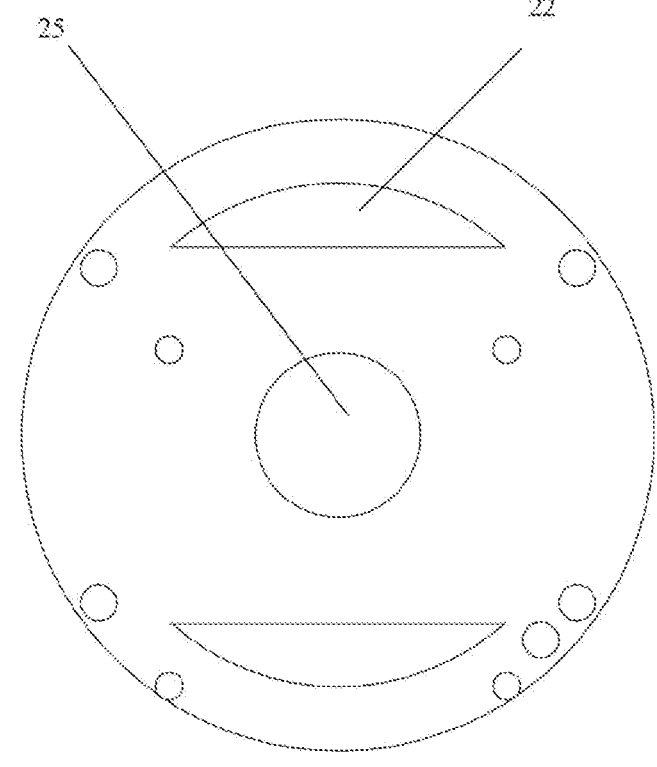
FIG. 12 is a top view of the fourth mounting plate of the in-situ testing instrument for soil moisture in a hole.
Figure 13:
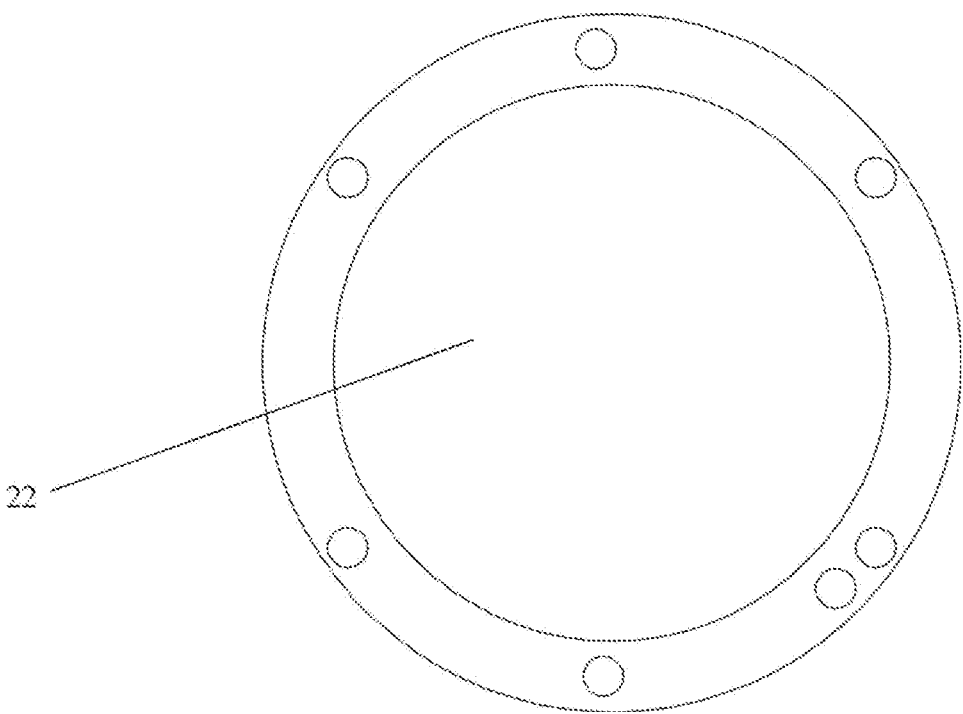
FIG. 13 is a top view of the fifth mounting plate of the in-situ testing instrument for soil moisture in a hole.

Among them: 1, the first mounting plate; 2, screw; 3, the second mounting plate; 4, the third mounting plate; 5, the fourth mounting plate; 6, the fifth mounting plate; 7, hanger; 8, rope; 9, handle; 10, support; 11, rotating shaft; 12, reel; 13, speed-regulating motor; 14, endoscope; 15, moisture sensor; 16, mounting shell; 161, left mounting semi-shell, 17, endoscope controller; 18, monitoring terminal; 19, moisture sensor reader; 20, power supply; 21, motor controller; 22, weight-reducing hole; 23, C-type sliding groove; 24, C-type guide groove; 25, motor shaft hole, 26, horizontal gear placing frame, 27, horizontal gear.

DETAILED DESCRIPTION OF THE
EMBODIMENTS

The following will further describe the invention in combination with the attached figures, it should be noted that this embodiment is based on this technical solution and gives a detailed embodiment and specific operation process, but the protection scope of the invention is not limited to this embodiment.

An in-situ testing instrument for soil moisture in a hole, comprising the test bracket extended into a hole, the retracting and releasing mechanism used to drive the test bracket to rise and fall in the hole, the moisture test mechanism arranged on the test bracket, the plug-and-pull drive mechanism used to drive the moisture test mechanism to insert into soil on the side of the hole or to be pulled out by the soil on the side of the hole, and the signal receiving mechanism arranged on the ground, the signal receiving mechanism is electrically connected with the moisture test mechanism.

Among them, the test bracket comprises the first mounting plate 1, the second mounting plate 3, the third mounting plate 4, the fourth mounting plate 5, and the fifth mounting plate 6 connected in turn by the screw 2 from the bottom to the top; the top of the fifth mounting plate 1 is connected to the lifting rope 8 of the retracting and releasing mechanism through the hanger 7.

Preferably, the retracting and releasing mechanism comprises the support 10 fixed on the ground, the rotating shaft 11 set inside the support 10 and the reel 12 fixed on the rotating shaft 11 at the position of the corresponding hole, one end of the rope 8 is wound on the reel 12, and the other end of the rope 8 is fixedly connected to the hanger 7; the rotating shaft 11 is fixed with the handle 9 at one end of the support 10, the support 10 comprises the bottom support seat and the cylinder fixed at the top of the bottom support seat, the cylinder is connected to the rotating shaft 11 through the bearing, so that the handle 9 drives the rotating shaft 11 to rotate 360° in the support 10.

Preferably, the moisture test mechanism comprises the mounting shell 16 set slidingly on the second positioning plate, the moisture sensor 15 fixed inside the mounting shell 16, and a probe fixedly connected to the main body of the moisture sensor 15 at one end, and the other end of the probe extends out of the mounting shell 16. In this embodiment, the mounting shell 16 comprises a left mounting semi-shell 161 and a right mounting semi-shell fixedly connected by screws, a mounting cavity for installing the main body of the moisture sensor 15 is arranged between the left mounting semi-shell 161 and the right mounting semi-shell, semi-circular perforation holes are set in the center of both ends, and the probe is pierced out of a circular hole composed of two semi-circular perforation holes, the top edge of the left mounting semi-shell 161 and the top edge of the right mounting semi-shell are fixed with the ear plate, the bolt is used to pass through the ear plate to connect the mounting shell 16 and the horizontal gear placing frame 26 of the plug-and-pull drive mechanism.

Preferably, the plug-and-pull drive mechanism comprises the speed-regulating motor fixed at the top of the fourth mounting plate 5, the vertical gear shaft which is in a keyed connection with an output shaft of the speed-regulating motor at one end, the horizontal gear 27 fixedly connected to the other end of the vertical gear shaft, and the horizontal gear placing frame 26 in which the inner side meshes with the outer side of the horizontal gear 27, the rack is fixed on the side in which the horizontal gear placing frame 26 meshes with the horizontal gear 27, thus the horizontal gear placing frame 26 is driven to move horizontally under the action of the horizontal gear 27 and the rack, the bottom end of the horizontal gear placing frame 26 is fixedly connected to the mounting shell 16, in this embodiment, the height of the horizontal gear placing frame 26 is equal to the height of the horizontal gear 27, so that the horizontal gear 27 is completely placed inside the horizontal gear placing frame 26, and the tooth parameters of the two components are the same to ensure a stable meshing.

The speed-regulating motor 13 is electrically connected with the motor controller 21 arranged on the ground to control the steering and speed of the speed-regulating motor 13.

Preferably, the center of the fourth mounting plate 5 is equipped with a motor shaft hole 25; the C-type guide groove 24 is opened in the middle of the third mounting plate 4, and the C-type sliding groove 23 is opened on the second mounting plate 3 and corresponding to the position of the C-type guide groove 24, the C-type guide groove 24 and the C-type sliding groove 23 open in the same direction; that is, the holes are opened toward the side wall of the holes; the groove wall of the C-type sliding groove 23 is protruded from the C-type guide groove 24, the mounting shell 16 is set horizontally and slidingly inside the C-type sliding groove 23, the horizontal gear placing frame 26 is set slidingly inside the C-type guide groove 24 at the top of the C-type sliding groove 23.

Preferably, weight-reducing holes are set at the center of the first mounting plate 1, the two sides of the second mounting plate 3, the two sides of the third mounting plate 4, the two sides of the fourth mounting plate 5, and the center of the fifth mounting plate 6, which is used to reduce the weight of the instrument.

Preferably, the endoscope 14 is fixed on the position on the screw 2 where corresponding to the moisture sensor 15; the endoscope 14 is electrically connected with an endoscope controller 17 arranged on the ground, and the endoscope controller 17 communicates with the monitoring terminal 18, the monitoring terminal 18 in this embodiment is a smartphone with an endoscope 14 video display APP, which is used to observe the position of the moisture sensor, thus, according to the position of the moisture sensor 15, the running state of the speed-regulating motor 13 is controlled.

Preferably, the signal receiving mechanism is the moisture sensor reader 19 arranged on the ground.

A method of the in-situ testing instrument for soil moisture in a hole comprises the following steps:

S1, the hole is drilled in the area to be detected;

S2, the retracting and releasing mechanism is placed on the ground corresponding to the hole, and the test bracket is placed inside the hole;

S3, the power supply 20 is turned on, the handle 9 is used to rotate the rotating shaft 11, and the test bracket is lowered until the probe on the test bracket reaches first test depth;

S4, the motor controller 21 controls the rotation of the speed-regulating motor 13, the speed-regulating motor 13 drives the horizontal gear 27 to rotate through the vertical gear shaft, and then drives the horizontal gear placing frame 26 to move in the direction of the C-type guide groove 24 towards the side wall of the hole, at the same time, the mounting shell drives the moisture sensor 15 to move in the direction of the C-type sliding groove 23 towards the side wall of the hole, the endoscope is used to observed until the probe of the moisture sensor 15 is inserted into the inside of the side wall of the hole, and the speed-regulating motor is stopped from rotating, at this time, the moisture sensor 15 is used to read the moisture information of the soil at the current depth, and the moisture information is transmitted to the moisture sensor reader 19, after finishing reading (In this embodiment, by reading the soil moisture content of the multiple times, an average value is taken as the hole wall soil moisture content), the motor controller 21 controls the speed-regulating motor to rotate reversely, the probe is drawn back to control the speed-regulating motor to stop running (The position of the moisture sensor 15, which is fed back by the endoscope 14 received by the smartphone, determines whether it is inserted into the soil or extracted from the soil);

S5, the rotating shaft 11 is rotated again, the test bracket is lowered until the probe on the test bracket reaches the second test depth, and S4 is repeated until the test is completed.

Therefore, the invention adopts the above-mentioned in-situ testing instrument and method for soil moisture in a hole. By in-situ testing the soil moisture content, the steps of taking soil, packaging, weighing, and drying are eliminated, and the test efficiency is improved. At the same time, the test accuracy is improved.

Finally, it should be explained that the above embodiment is only used to illustrate the technical solution of the invention rather than to restrict it. Although the invention is described in detail concerning the better embodiment, the ordinary technical personnel in this field should understand that they can still modify or replace the technical solution of the invention, and these modifications or equivalent substitutions cannot make the modified technical solution break away from the spirit and encirclement of the technical solution of the invention.

What is claimed is:

1. An in-situ testing instrument for soil moisture in a hole, comprising:
    a test bracket extended into the hole,
    a retracting and releasing mechanism used to drive the test bracket to rise and fall in the hole,
    a moisture test mechanism arranged on the test bracket,
    a plug-and-pull drive mechanism used to drive the moisture test mechanism to insert into soil on a side of the hole or to be pulled out by the soil on a side of the hole, and
    a signal receiving mechanism arranged on a ground, wherein the signal receiving mechanism is electrically connected with the moisture test mechanism;
    wherein the test bracket comprises a first mounting plate, a second mounting plate, a third mounting plate, a fourth mounting plate, and a fifth mounting plate connected in turn by a screw from a bottom to a top;
    a top of the fifth mounting plate is connected to a lifting rope of the retracting and releasing mechanism through a hanger.

2. The in-situ testing instrument according to claim 1, wherein the retracting and releasing mechanism comprises a support fixed on the ground, a rotating shaft set inside the support, and a reel fixed on the rotating shaft at a position of a corresponding hole, a first end of the lifting rope is wound on the reel, and a second end of the lifting rope is fixedly connected to the hanger;
    one end of the rotating shaft passes through the support and is fixed with a handle.

3. The in-situ testing instrument according to claim 1, wherein the moisture test mechanism comprises a mounting shell set slidingly on a positioning plate, a moisture sensor fixed inside the mounting shell, and a probe having a first end fixedly connected to the moisture sensor, and a second end extending out of the mounting shell.

4. The in-situ testing instrument according to claim 3, wherein the plug-and-pull drive mechanism comprises a speed-regulating motor fixed at a top of the fourth mounting plate, a vertical gear shaft having a first end in a keyed connection with an output shaft of the speed-regulating motor, a horizontal gear fixedly connected to a second end of the vertical gear shaft, and a horizontal gear placing frame, wherein an inner side of the horizontal gear placing frame meshes with an outer side of the horizontal gear;

the speed-regulating motor is electrically connected with a motor controller arranged on the ground.

5. The in-situ testing instrument according to claim 4, wherein a center of the fourth mounting plate is equipped with a motor shaft hole;

a C-type guide groove is opened in a middle of the third mounting plate, and a C-type sliding groove is opened on the second mounting plate and corresponding to a position of the C-type guide groove, the C-type guide groove and the C-type sliding groove open in a same direction;

a groove wall of the C-type sliding groove is protruded from the C-type guide groove, the mounting shell is set horizontally and slidingly inside the C-type sliding groove, and the horizontal gear placing frame is set slidingly inside the C-type guide groove at a top of the C-type sliding groove.

6. The in-situ testing instrument according to claim 4, wherein weight-reducing holes are set at a center of the first mounting plate, two sides of the second mounting plate, two sides of the third mounting plate, two sides of the fourth mounting plate, and a center of the fifth mounting plate.

7. The in-situ testing instrument according to claim 4, wherein an endoscope is fixed on a position on the screw where corresponding to the moisture sensor; the endoscope is electrically connected with an endoscope controller arranged on the ground, and the endoscope controller communicates with a monitoring terminal to observe a position of the moisture sensor.

8. The in-situ testing instrument according to claim 3, wherein the signal receiving mechanism is a moisture sensor reader arranged on the ground.

9. A testing method by using the in-situ testing instrument according to claim 1, comprising:

S1, drilling a hole in an area to be detected;

S2, placing the retracting and releasing mechanism on the ground corresponding to the hole, and placing the test bracket inside the hole;

S3, turning on a power supply, using a handle to rotate a rotating shaft, and lowering the test bracket until a probe on the test bracket reaches a first test depth;

S4, controlling a rotation of a speed-regulating motor by a motor controller, driving a horizontal gear to rotate through a vertical gear shaft by the speed-regulating motor, and then driving a horizontal gear placing frame to move in a direction of a C-type guide groove towards a side wall of the hole, at a same time, driving a moisture sensor to move in a direction of a C-type sliding groove towards a side wall of the hole by a mounting shell, observing by an endoscope until a probe of the moisture sensor is inserted into the inside of the side wall of the hole, and stopping the speed-regulating motor from rotating, at this time, reading moisture information of the soil at a current depth by the moisture sensor and transmitting the moisture information to a moisture sensor reader, after finishing reading, controlling the speed-regulating motor to rotate reversely by the motor controller, drawing back the probe to control the speed-regulating motor to stop running; and S5, rotating the rotating shaft again, lowering the test bracket until the probe on the test bracket reaches a second test depth, and repeating S4 until the test method is completed;

wherein in the in-situ testing instrument, the test bracket comprises a first mounting plate, a second mounting plate, a third mounting plate, a fourth mounting plate, and a fifth mounting plate connected in turn by a screw from a bottom to a top; a top of the fifth mounting plate is connected to a lifting rope of the retracting and releasing mechanism through a hanger.

10. The testing method according to claim 9, wherein in the in-situ testing instrument, the retracting and releasing mechanism comprises a support fixed on the ground, the rotating shaft set inside the support, and a reel fixed on the rotating shaft at a position of a corresponding hole, a first end of the lifting rope is wound on the reel, and a second end of the lifting rope is fixedly connected to the hanger;

one end of the rotating shaft that passes through the support is fixed with the handle.

11. The testing method according to claim 9, wherein in the in-situ testing instrument, the moisture test mechanism comprises a mounting shell set slidingly on a positioning plate, the moisture sensor fixed inside the mounting shell, and the probe having a first end fixedly connected to the moisture sensor, and a second end extending out of the mounting shell.

12. The testing method according to claim 11, wherein in the in-situ testing instrument, the plug-and-pull drive mechanism comprises the speed-regulating motor fixed at a top of the fourth mounting plate, the vertical gear shaft having a first end in a keyed connection with an output shaft of the speed-regulating motor, the horizontal gear fixedly connected to a second end of the vertical gear shaft, and the horizontal gear placing frame, wherein an inner side of the horizontal gear placing frame meshes with an outer side of the horizontal gear;

the speed-regulating motor is electrically connected with the motor controller arranged on the ground.

13. The testing method according to claim 12, wherein in the in-situ testing instrument, a center of the fourth mounting plate is equipped with a motor shaft hole;

the C-type guide groove is opened in a middle of the third mounting plate, and the C-type sliding groove is opened on the second mounting plate and corresponding to a position of the C-type guide groove, the C-type guide groove and the C-type sliding groove open in a same direction;

a groove wall of the C-type sliding groove is protruded from the C-type guide groove, the mounting shell is set horizontally and slidingly inside the C-type sliding groove, and the horizontal gear placing frame is set slidingly inside the C-type guide groove at a top of the C-type sliding groove.

14. The testing method according to claim 12, wherein in the in-situ testing instrument, wherein weight-reducing holes are set at a center of the first mounting plate, two sides of the second mounting plate, two sides of the third mounting plate, two sides of the fourth mounting plate, and a center of the fifth mounting plate.

15. The testing method according to claim 12, wherein in the in-situ testing instrument, an endoscope is fixed on a position on the screw where corresponding to the moisture sensor; the endoscope is electrically connected with an endoscope controller arranged on the ground, and the endoscope controller communicates with a monitoring terminal to observe a position of the moisture sensor.

16. The testing method according to claim 11, wherein in the in-situ testing instrument, the signal receiving mechanism is the moisture sensor reader arranged on the ground.

\* \* \* \* \*